United States Patent
Kassab et al.

(10) Patent No.: US 10,213,207 B2
(45) Date of Patent: *Feb. 26, 2019

(54) SEPTAL OCCLUSION DEVICES AND METHODS

(71) Applicant: CVDevices, LLC, San Diego, CA (US)

(72) Inventors: Ghassan S. Kassab, La Jolla, CA (US); Jose A. Navia, Sr., Buenos Aires (AR)

(73) Assignee: CVDevices, LLC, San Diego, CA (US)

( * ) Notice: Subject to any disclaimer, the term of this patent is extended or adjusted under 35 U.S.C. 154(b) by 372 days.

This patent is subject to a terminal disclaimer.

(21) Appl. No.: 14/955,967

(22) Filed: Dec. 1, 2015

(65) Prior Publication Data

US 2016/0081695 A1 Mar. 24, 2016

Related U.S. Application Data (63) Continuation of application No. 11/997,150, filed as application No. PCT/US2006/029224 on Jul. 28, 2006, now Pat. No. 9,198,646.

(60) Provisional application No. 60/703,421, filed on Jul. 29, 2005.

(51) Int. Cl.
*A61B 17/12* (2006.01)
*A61B 17/00* (2006.01)

(52) U.S. Cl.
CPC .... *A61B 17/12122* (2013.01); *A61B 17/0057* (2013.01); *A61B 17/12022* (2013.01); *A61B 2017/00575* (2013.01); *A61B 2017/00592* (2013.01); *A61B 2017/00606* (2013.01); *A61B 2017/00619* (2013.01); *A61B 2017/00876* (2013.01)

(58) Field of Classification Search
CPC .......... A61B 17/0057; A61B 17/12122; A61B 2017/00575; A61B 2017/00592; A61B 2017/00597; A61B 2017/00606; A61B 2017/00615; A61B 2017/00619; A61B 2017/00623

See application file for complete search history.

(56) References Cited

U.S. PATENT DOCUMENTS

| | | | | |
|---|---|---|---|---|
| 5,421,825 A * | 6/1995 | Farcot | ............... | A61M 25/0662 604/284 |
| 6,596,013 B2 * | 7/2003 | Yang | ................... | A61B 17/0057 606/139 |
| 6,719,768 B1 * | 4/2004 | Cole | ................... | A61B 17/0057 606/153 |
| 9,198,646 B2 * | 12/2015 | Kassab | ............... | A61B 17/0057 |
| 2011/0213413 A1 * | 9/2011 | Brown | ............... | A61B 5/02014 606/213 |

* cited by examiner

*Primary Examiner* — Todd Scherbel
(74) *Attorney, Agent, or Firm* — Reichel Stohry LLP; Mark C. Reichel; Natalie J. Dean (57) ABSTRACT

A magnetic device and method are disclosed for providing a safer and more reliable technique for closing a hole or rupture in the septum of the heart. A device is disclosed with proximal and distal occluders that are connected to one another via a catheter and are inserted on either side of the hole or rupture. Also disclosed are two patches that are placed on either side of the hole or rupture with at least one of the patches being composed of magnetic material with the other being magnetic or metallic.

18 Claims, 7 Drawing Sheets

SEPTAL OCCLUSION DEVICES AND METHODS

PRIORITY

The present application is related to, claims the priority benefit of, and is a U.S. continuation application of, U.S. patent application Ser. No. 11/997,150, filed Aug. 11, 2008 and issued as U.S. Pat. No. 9,198,646 on Dec. 1, 2015, which is related to, claims the priority benefit of, and is a U.S. National Stage Application of, International Patent Application Ser. No. PCT/US2006/029224, filed Jul. 28, 2006, which is related to, and claims the priority benefit of, U.S. Provisional Patent Application Ser. No. 60/703,421, filed Jul. 29, 2005. The contents of each of these applications and patent are hereby incorporated by reference in their entirety into this disclosure.

BACKGROUND OF THE INVENTION

1. Field of the Invention

The present invention relates generally to occluding the septum of the heart. More particularly, the present invention relates to magnetic devices and method which can be used to occlude holes or ruptures in the atrial and ventricular septa of the heart.

2. Background of the Invention

There are many congenital defects that may be present in human beings. Of such defects, atrial septal defects (ASDs) are congenital abnormalities characterized by an alteration in the structure of the atrial septum. The frequency of these abnormalities is about 10% of all congenital heart disease, with a 3:2 female/male ratio.

The physiological outcome of an atrial septal defect is influenced by the size of the ASD and duration of the shunt, and on the reaction of the pulmonary vascular bed. In large ASDs with significant left-to-right shunts, the defect produces an important volume-overloaded in the right atrium and right ventricle, with an increased volume ejected into a low-resistance pulmonary vascular bed. This may result in the development in adulthood of pulmonary vascular occlusive disease and pulmonary arterial hypertension. The rate of survival in young adults when they develop progressive pulmonary hypertension is limited.

Patients diagnosed as having secundum ASDs with a significant shunt (defined as a pulmonary blood flow to systemic blood flow ratio (Qp/Qs) of >1.5) are operated upon ideally before 5 years of age or whenever a diagnosis is made in later years. In the past, cardiac catheterization oximetry measurement was performed to evaluate the magnitude of left-to-right shunt. Currently, two-dimensional echocardiography and Doppler color flow mapping is typically used to visualize the anatomy of the defect and estimate the Qp/Qs ratio from Doppler indices.

ASDs are classified by size: small defects with a maximal diameter >3 mm to <6 mm, moderate defects measured ≥6 mm to <12 mm and large defects were ≥12 mm. Two thirds of the ASDs secundum type may increase as time goes by. This makes them candidates for transcatheter closure with specific devices. ASD is the second most common congenital heart lesion in adult and children as well.

Transcatheter closures for atrial septal defects were performed for the first time in experimental animal models and humans by King and Mills. Some researchers developed a single disk-device with tethering hooks but the implantation was difficult. The two devices currently undergoing evaluation, the Lock "clamshell" device and the Sideris "buttoned" device are essentially umbrella-like devices for supporting the fabric patches. Problems with the clamshell device include spontaneous device embolization, persistent residual shunts in as many as 26% of patients and wire fractures in up to 33% of patients on follow-up. Nowadays, Amplatzer symmetric and an asymmetric mechanical occluder are under current medical use.

A patent foramen ovale (PFO) is a persistent defect, usually a flap-like opening between the atrial septum primum and secundum at the location of the fossa ovalis. The foramen ovale is utilized during intrauterine life as a physiologic conduit for right-to-left blood shunting. Functional closure of the foramen ovale occurs after birth, once the pulmonary circulation has been established increasing left atrial blood flow and pressure. The persistence of patent foramen ovale has been found between 25-35% of adults in an autopsy series without a gender preference. Echocardiography is a method through which PFO can be detected in vivo in 5-20% in the adult population.

One of the major complications of PFO could be paradoxical embolism which is thought to be responsible for an embolic event in the absence of a left-sided thromboembolic source, the potential for right-to-left shunting, and the detection of thrombus in the venous system or right atrium.

The diagnosis of paradoxical embolism is usually presumptive. Its mechanisms are believed to be caused by: a chronic elevation of right atrial pressure with consecutive right-to-left shunt (e.g., pulmonary hypertension, COPD, pulmonary embolism), or a transient elevation of right atrial pressure after release of positive airway pressure (Valsalva, cough, diving).

A retrospective French multicenter study reported a yearly risk of 1.2% to sustain a recurrent TIA, and of 3.4% to suffer a recurrent stroke or TIA; this was despite medical treatment with oral anticoagulants or antiplatelet drugs in patients with PFO and cryptogenic stroke.

Nonsurgical closure of PFOs has become possible with the advent of transcatheter closure devices, initially developed for percutaneous closure of atrial septal defects (ASD).

Ventricular septal defect (VSD) is the most common congenital heart disease (approximately 20%). The perimembranous (PmVSD) defect, involving the membranous septum and the adjacent area of muscular septum is presented in about 70% of all VSD. Surgical repair is the most common treatment with low postoperative mortality but still with potential risks of complete heart block, chylothorax, phrenic nerve injury, early and late arrhythmias, postpericardiotomy syndrome, wound infection, and neurologic sequelae of cardiopulmonary bypass.

The failure of different devices to occlude the VSD were related to large delivery sheaths (11-F) required, complex implantation techniques, inability to reposition and redeploy the device, and mainly interference with the aortic and tricuspid valves and significant residual shunts (25% to 60%). The criteria to include the closure of PmVSD include, but are not limited to: echocardiographic studies, symptoms of heart failure or evidence of left atrial and or left ventricular enlargement.

The Amplatzer Membranous VSD Occluder is the only device currently used specifically designed for PmVSDs occlusion. However, this device typically cannot be used if: 1) body weight <8 kg, 2) subaortic rim as shown by echocardiography in the long-axis view <2 mm, 3) left ventricle to right atrial shunting, 4) right to left shunting through the defect, 5) PmVSD with an aneurysm and multiple shunts that could not be successfully closed with one device, 6) sepsis, 7) complex heart lesions such as tetralogy of Fallot, 8) contraindication to antiplatelet therapy.

During myocardial infarction, ventricular septal rupture can occur. Ventricular septal rupture is one of at least three mechanical complications that can occur following myocardial infarction. The septal rupture can result from full thickness infarction of the interventricular septum followed by enough necrosis to result in the septal rupture. Others myocardial infarction complications are free wall rupture, and papillary muscle rupture. Free wall rupture usually results in rapid death while papillary muscle rupture results in sudden mitral regurgitation.

At present with thrombolysis treatment in acute myocardial infarction and early intervention, the incidence of postinfarction ventricular septal rupture has diminished from the 1-3% to 0.2%. The risk factors associated with this severe complication (IVSR) include advanced age, anterior infarction, female gender and smoking history and lack of collateral circulation.

The post AMI ventricular septal rupture can be divided into simple and complex. In the former, the rupture connects the two ventricles without gross hemorrhage or muscle laceration and with the opening between right and left ventricle at the same horizontal level of the ventricular septum. This is more frequent in the anterior infarct. In the latter, the interventricular communication presents a convoluted course with a tract that might extend into regions remote from the primary AMI site. This rupture is more complex due to the presence of hemorrhage, disruption of myocardial muscle and multiple perforations. This often occurs in multiple vessel disease and inferior myocardial infarction.

In a GUSTO-I (global utilization of streptokinase and t-PA for occluded coronary arteries) trial there was an incidence of 0.2% of ventricular septal rupture in over 41,000 patients, a 5-10 fold reduction as compared with the pre-thrombolytic era. Nowadays, the average time interval between infarction and rupture is nearly one day, while before the thrombolytic area it was between 5-6 days. However, the surgical mortality ultimately has increased maybe due to the change in the patient population. At present, the thrombolytic treatment may augment the complex rupture portion which is more difficult to repair surgically, instead of the simple ruptures. Moreover, patients in the first 24-48 hours after infarction are less likely to sustain the surgical trauma than they would be a week or so later.

The post-myocardial septal rupture consequence is the shunting of oxygenated blood from the left to the right ventricle. The right ventricle, generally involved in the infarct, suffers an augmented volume load. The factors that are related with poor outcome are hypotension, oliguria, elevated creatinine, and cardiogenic shock to be associated with non-survivors. A multivariate analysis demonstrated that increasing age, anterior infarction, and female sex as predictors of ventricular septal rupture. When the right ventricular is involved in the infarction the outcome is generally poor—only about 24% with poor right ventricular free wall contraction survived compared to about 80% survival with a good right ventricular function.

The GUSTO-I study trial showed that patients treated surgically had a 47% mortality rate within a 30 day period while for non surgical patients mortality rate was 94%. In the SHOCK trial the hospital patients with cardiogenic shock who underwent surgical repair of ventricular septal rupture mortality was 81%.

The surgical principles for occlusion of VSR include hypothermia during cardiopulmonary bypass with myocardial protection, trans-infarction approach to the VSR, trimming of infarcted muscle around the VSR, closure of the VSR with a patch to avoid tension, closure of the ventricle without tension with buttressed sutures.

In spite of these surgical measurements, the residual or recurrent ventricular septal defect following initial surgical repair was as high as 20% of the cases due to the infarct extension leading to patch dehiscence or creation of a new VSD.

Another option is transcatheter closure of VSR, which is exigent because the patients are seriously ill. Moreover, patients referred for transcatheter closure have generally been rejected for surgical closure due to cardiogenic shock or advanced age.

So far, ventricular septal rupture repair continues to be a challenge. There have only been a few single case reports and small series. Others reported successful closure, using an Amplatzer septal occluder, of a residual defect following surgical patch closure.

Others have suggested that device closure may provide temporary stabilization of the haemodynamic alteration. This may allow surgical closure after the infarcted myocardium around the rupture has had time to fibrose. With the current devices, closure is most difficult while the margins of the rupture are soft and necrotic.

SUMMARY OF THE INVENTION

The current devices and methods for closing a hole or rupture in the heart are unreliable and may require extensive post-operative work to re-establish normal cardiac functioning. The present invention provides a safer magnetic device and method for closing septal holes or ruptures which are not subject to the problems associated with the current devices and methods such as migration, cardiogenic shock, exacerbation, etc.

In one exemplary embodiment, the present invention is a magnetic device for controlling the leakage of a septum in a heart. The device includes a proximal occluder and distal occluder with magnetic properties; a catheter; a covering, and a stabilizer, wherein the proximal occluder is connected to the catheter at a proximal end and the distal occluder is situated further down the body of the catheter.

In another exemplary embodiment, the present invention is a magnetic device for controlling the leakage of a septum in a heart. The device includes a first patch with magnetic properties positioned within a lumen of a heart cavity; a second patch with magnetic properties positioned within a lumen of another heart cavity; and wherein the first patch and the second patch are positioned on adjacent sides of a portion of the septum in the heart.

In yet another exemplary embodiment, the present invention is a method for magnetic tissue support. The method includes introducing a metallic body on one side of a heart tissue that needs support; and introducing a magnet on the opposite side of a heart tissue that needs support so that the magnet and the metallic body form an attractive force across the body of the tissue that needs support, thereby providing support to the tissue.

As used herein and throughout this application, "proximal" is used to refer to a region of the present invention which is inserted first into the target tissue and therefore closer to the target tissue during insertion and "distal" is used to refer to a position closer to the region of the present invention which is farther away from the target tissue during insertion of the present invention.

DETAILED DESCRIPTION OF THE INVENTION

The present invention includes magnetic devices and methods used for occluding a hole or rupture in body tissue such that there is minimized to no fluid communication between the sides partitioned by the body tissue. In particular embodiments and examples presented herein, such magnetic devices and methods are described with respect to occluding a hole or rupture in the septum of the heart but it must be noted that such magnetic devices and methods according to the present invention are not limited to the septum of the heart alone but may be applicable to any body tissue that could benefit from the use of such magnetic devices and methods. Furthermore, the present invention allows for more efficient and more secure treatment of tissue leakage to increase the safety and reliability of minimally invasive correctional procedures.

Figure 1:
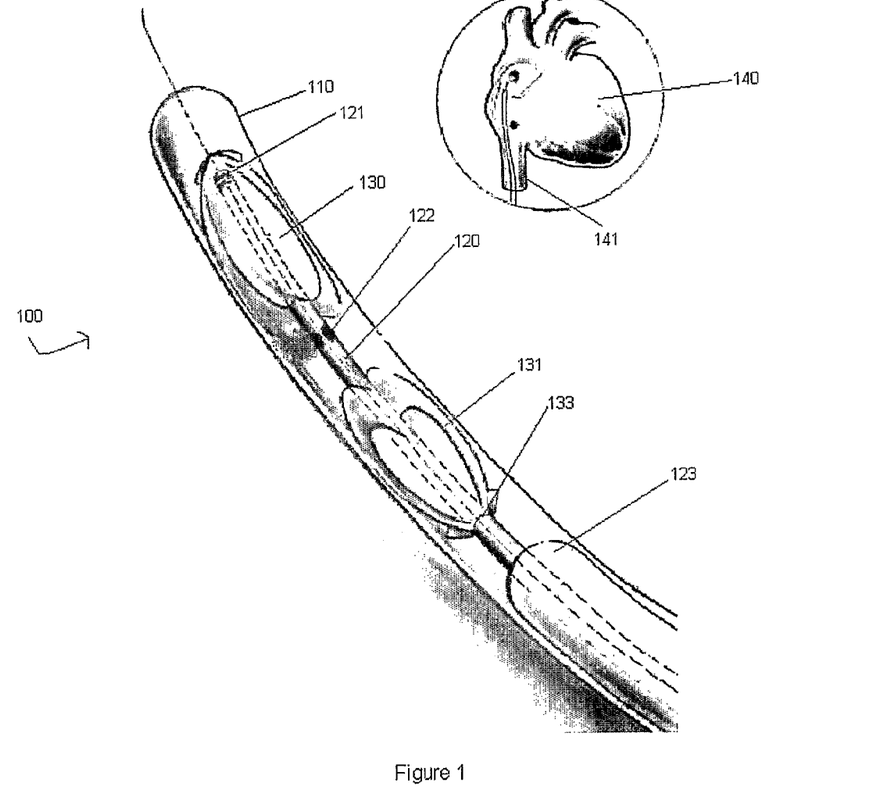
FIG. 1 shows a front view of a magnetic device including proximal and distal magnetic occluders according to an exemplary embodiment of the present invention, with the top, right panel showing the venous access to the atrium.

An exemplary embodiment of the present invention as used in magnetic assembly 100 is shown in FIG. 1. Assembly 100 includes a proximal magnetic occluder 130, a distal magnetic occluder 131, catheter 120 with openings 122, catheter screw tip 121, covering 110, and stabilizer 123. The proximal magnetic occluder 130 and distal magnetic occluder 131 function to seal off a hole or rupture in the target tissue (e.g., septum of the heart) and thereby provide support for the tissue and prevent fluid communication across its body.

The proximal magnetic occluder 130 and distal magnetic occluder 131 may be disk-shaped as illustrated in FIG. 1 or they may be of any other shape (e.g., elliptical, rectangular, etc.) such that it can effectively function to occlude and seal a uniquely defined hole or rupture in the target tissue. The proximal magnetic occluder 130 and distal magnetic occluder 131 may also be of other conformations including but not limited to rings, radial extensions, stents, umbrellas and the like. They may also be covered with Dacron, polytetrafluoroethylene, polyurethane, biological tissue (e.g., pericardium), or reabsorbable polymers on its surface. They may be composed entirely of any suitable pliable magnetic material commonly used in the medical arts or they may only be composed of pliable magnetic material on the inner surfaces physically contacting the target tissue. Different sizes may also be used according to the echo dimension and patient specific shape of the hole or rupture in the target tissue. The proximal magnetic occluder 130 and distal magnetic occluder 131 may be pliable such that they can assume the compressed shape illustrated in FIG. 1 when the covering 110 surrounds them. They may also be resilient enough to assume the expanded form as shown in later figures once exposed. In this way, the proximal magnetic occluder 130 and distal magnetic occluder 131 can be maintained inside the covering 110 during insertion of assembly 100 into the patient's heart in order for assembly 100 to pass smoothly and unimpeded into the target tissue.

The proximal magnetic occluder 130 and the distal magnetic occluder 131 may possess threaded throughbores 133 in the center of their bodies of a diameter slightly larger than the diameter of catheter 120 such that the catheter 120 is able to slide smoothly and controllably through the threaded throughbores 133 after successful positioning of the proximal magnetic occluder 130 and the distal magnetic occluder 131. The proximal magnetic occluder 130 and the distal magnetic occluder 131 may also possess barbs or projections (not shown) emanating from their surfaces such that when positioned on either side of the target tissue the two occluders may be more securely held in place. In the unused form of assembly 100, the catheter screw tip 121 may be connected to and screwed into the threaded throughbore 133 of proximal magnetic occluder 130.

The covering 110 may serve a protective function by securing the proximal magnetic occluder 130 and distal magnetic occluder 131 within the body of covering 100 thereby preventing premature contact with healthy tissue. The catheter 120 may possess a catheter screw tip 121 at its proximal end just distal to the distal surface of proximal magnetic occluder 130. The catheter screw tip 121 may be used to unscrew the proximal magnetic occluder 130 and distal magnetic occluder 131 from the catheter 120 after positioning them on either side of the damaged target tissue The catheter screw tip 121 may be non-magnetic in order to avoid opposing magnetic forces during removal of the catheter 120 after successful positioning of the proximal magnetic occluder 130 and distal magnetic occluder 131. The catheter 120 may be of a slightly smaller diameter than the diameter of the stabilizer 123 such that the catheter is able to pass smoothly but controllably within the stabilizer 123. The covering 110 and catheter 120 may be used to guide the attached proximal magnetic occluder 130 and distal magnetic occluder 131 through the inferior vena cava 141 of the heart 140 to the target tissue as shown in FIG. 1.

The stabilizer 123 may be of a diameter slightly smaller than the diameter of the covering 110 such that the stabilizer 123 is able to pass smoothly but controllably within the covering 110. Also, when the catheter 120 is guided into the target tissue, the stabilizer 123 may prevent the catheter 120 from shifting around the inside of covering 110. In this way, the operator's dexterity of the catheter 120 and the proximal magnetic occluder 130 and distal magnetic occluder 131 is augmented. Additionally, the catheter 120 may contain openings 122 in order to extract a blood sample to measure, for example, the oxygen saturation levels of blood in the target tissue to confirm the existence of some residual shunt. They may be situated at the proximal end of catheter 120 as shown in FIG. 1. Instead of openings 122, the catheter 120 may contain an oxygen sensor (not shown) which could analyze the $O_2$ saturation within the target tissue (e.g. via spectrophotometry) and would relay this information to a communication device (not shown) situated external to the patient's body via a wireless system (not shown) such as BLUETOOTH technology or other telemetry unit. In this way, it would be easier to ascertain data on the blood since no blood sample would have to be extracted in order to determine the $O_2$ saturation of blood in the target tissue.

This variation of the present invention may be used to discern the extent of the hole or rupture in the septum. For example, if the assembly 100 is first inserted into the left atrium of the heart, then a lower $O_2$ saturation value than would be normally expected would indicate that some of the deoxygenated blood from the right atrium of the heart may be leaking into the left atrium. The extent of the defect or damage to the tissue may thus be discerned by comparing the value of the observed $O_2$ saturation with the value of the expected $O_2$ saturation level. The openings 122 or the oxygen sensor (not shown) may be situated as shown in FIG. 1 just distal to the proximal magnetic occluder 130 and on a sufficient length of catheter 120 such that when the catheter 120 reaches the target blood sample, the openings 122 or the oxygen sensor (not shown) may contact the target blood sample without allowing the distal magnetic occluder 131 the opportunity to deploy as described further below.

The above described exemplary embodiment of the present invention may be used specifically to percutaneously (e.g., through internal jugular or femoral vein approach) close congenital defects such as ASD, PFO, and VSD, and it may also be delivered endovascularly. A number of advantage are evident using the present process, including but not limited to: 1) easy insertion under angiography, TE Eccho or intracardiac echo, 2) can be tailored to different sizes and shapes, 3) magnetic self supported, 4) disk covered with Dacron, PTFE, polyurethane, biologic tissue, reabsorbable polymers, 5) easy to deploy, 6) easy to align, and 7) extremely flat device to prevent interference with cardiac structures (coronary sinus, tricuspid valve, aortic valve, etc.).

The following description involves detailing the steps that may be used to implant the above described exemplary embodiment of the present invention. For sake of simplicity, the corresponding labeled regions in FIGS. 2 through 6 may not be redefined in each separate description of the figures and it should be assumed that the corresponding labels found in FIGS. 2 through 6 are subject to the same parameters and limitations as initially described in the description of FIG. 1.

Figure 2:
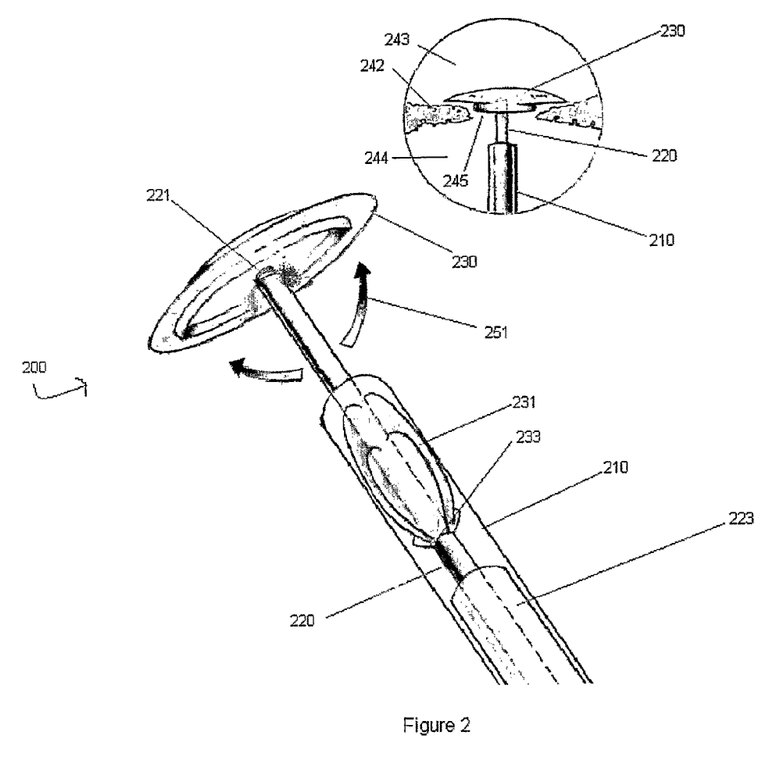
FIG. 2 shows a front view of a magnetic device with a proximal magnetic occluder being deployed after a catheter is advanced through the covering according to an exemplary embodiment of the present invention.

The next step of use of an exemplary embodiment of the present invention as used in a magnetic assembly 200 is shown in FIG. 2. After the septum 242 of the heart is reached via catheterization, assembly 200 may be guided through the hole or rupture 245 such that the proximal portion of assembly 200 and the proximal magnetic occluder 230 are pushed past the hole or rupture 245 and into the interior of the left atrium or ventricle 243 as shown in FIG. 2. In the event that the proximal portion of assembly 200 and the proximal magnetic occluder 230 can not fit through the hole or rupture 245, then a needle (not shown) may be used to poke through the hole or rupture 245 and enlarge it enough so that the proximal portion of assembly 200 and the proximal magnetic occluder 230 can pass through. Once the compressed proximal magnetic occluder 230 is pushed past the hole or rupture 245, the catheter 220 may be pushed forward and the covering 210 may be held in place such that the compressed proximal magnetic occluder 230 is exposed from the inside of covering 210. Then, the proximal magnetic occluder 230 may assume a disk-shape as illustrated by arrows 251. As described above, the proximal magnetic occluder 230 can be easily guided through the hole or rupture 245 while maintained inside the covering 210 in a compressed arrangement. When the proximal magnetic occluder 230 is positioned on past the septum 242, the user may advance the catheter 220 while holding the covering 210 to expose the proximal magnetic occluder 230 and allows it to assume the shaped as depicted in FIG. 2. The user may then pull back on assembly 200 such that the proximal magnetic occluder 230 is securely anchored to the surface of the septum 242 on the left atrial or ventricular 243 side. The edges of the proximal magnetic occluder 230 may reside on said surface before the user moves onto the next step in the implantation of the exemplary embodiment.

Figure 3:
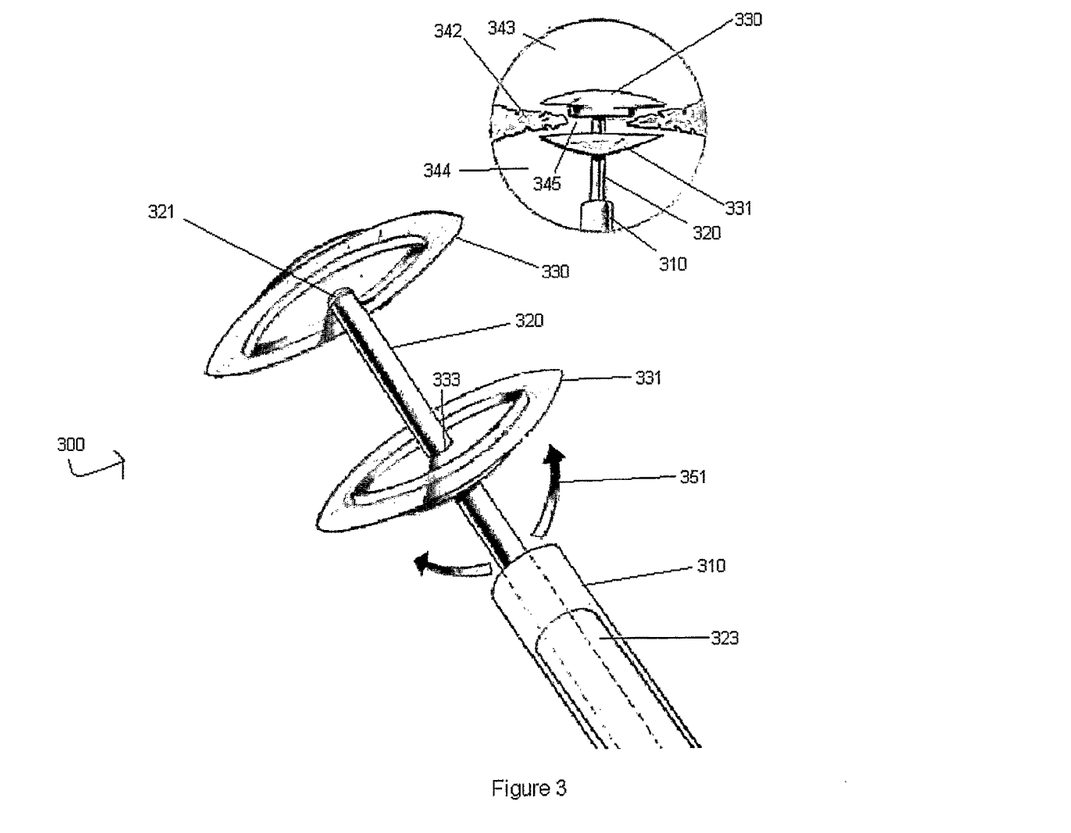
FIG. 3 shows a front view of a magnetic device with a distal magnetic occluder being deployed after a catheter is advanced through the covering according to an exemplary embodiment of the present invention.

The next step of use of an exemplary embodiment of the present invention as used in a magnetic assembly 300 is shown in FIG. 3. After the proximal magnetic occluder 330 is positioned as shown in FIG. 3, the user may advance the catheter 320 further while holding in place the covering 310 such that the distal magnetic occluder 331 is exposed form underneath the covering 310. Once exposed, the distal magnetic occluder 331 may assume the disk-shape as illustrated in FIG. 3 via an expanding process as illustrated by arrows 351. The proximal magnetic occluder 330 and the distal magnetic occluder 331 may be spaced apart such that the distance between them is at least equivalent to the thickness of the septum 342. In this way, when the distal magnetic occluder 331 is exposed, it is already in a position distal to the hole or rupture 345 and on or just distal to the surface of the septum 342 on the right atrial or ventricular 344 side. Thus, the proximal magnetic occluder 330 and the distal magnetic occluder 331 may be situated on either side of the hole or rupture 345 as shown in FIG. 3.

Figure 4:
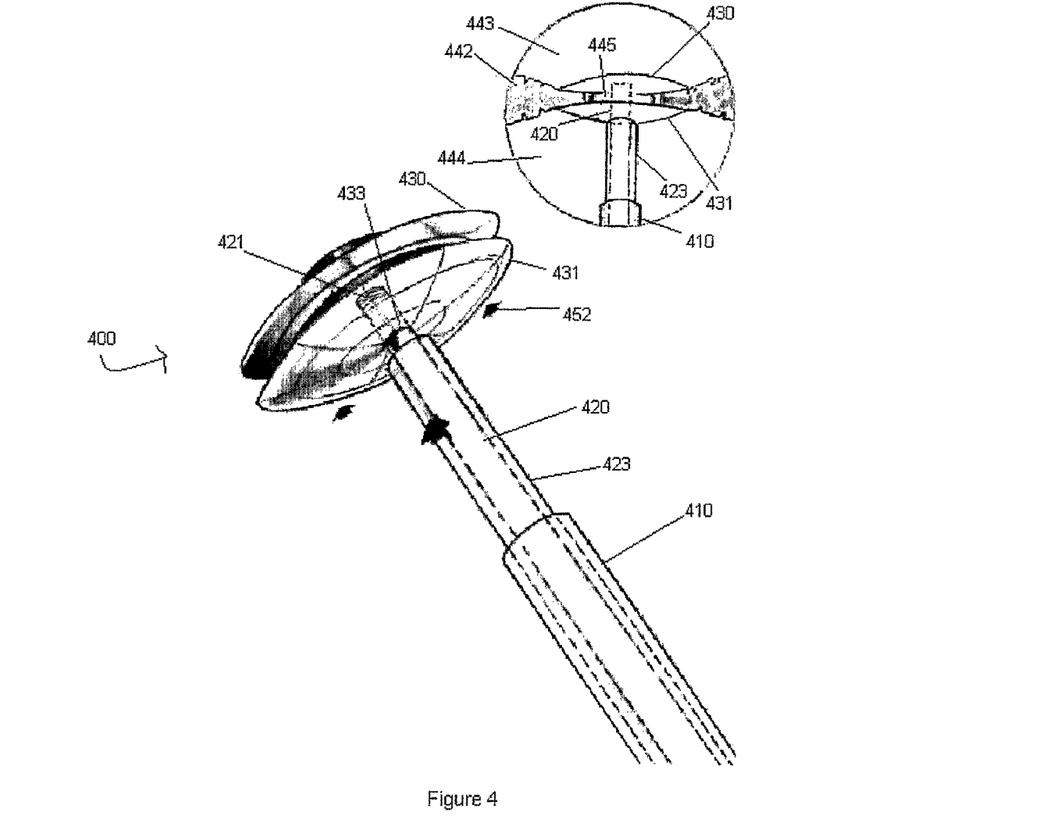
FIG. 4 shows a front view of a magnetic device with proximal and magnetic occluders in attractive communication with one another so as to "sandwich" the septal hole or rupture according to an exemplary embodiment of the present invention.

The next step of use of an exemplary embodiment of the present invention as used in a magnetic assembly 400 is shown in FIG. 4. After both the proximal magnetic occluder 430 and the distal magnetic occluder 431 are positioned on either side of the septum 442, the user may advance the stabilizer 423 in the direction of arrows 452 while holding in place the covering 410 of assembly 400 in order to clamp down and "sandwich" the hole or rupture 445 as illustrated in FIG. 4. In this way, the distal magnetic occluder 431 may be pushed proximally down the catheter 420 such that it may form a tight seal with the surface of the septum 442 on the right atrial or ventricular 444 side. The proximal magnetic occluder 430 and the distal magnetic occluder 431 thus form a leak-free barrier to reinforce the septum 442 and are held in place by the magnetic force each applies to the other. This magnetic force may be powerful enough to hold the proximal magnetic occluder 430 and the distal magnetic occluder 431 in place as shown in FIG. 4, and it may be of such magnitude that the magnetic occluders resist any shifting or sliding motion along the surface of the septum 442. Also, the magnetic force between the proximal magnetic occluder 430 and the distal magnetic occluder 431 may be of a magnitude such that the surfaces contacting the septum 442 are held and secured tightly enough to resist any fluid leakage between the left atrium or ventricle 443 and the right atrium or ventricle 444.

Figure 5:
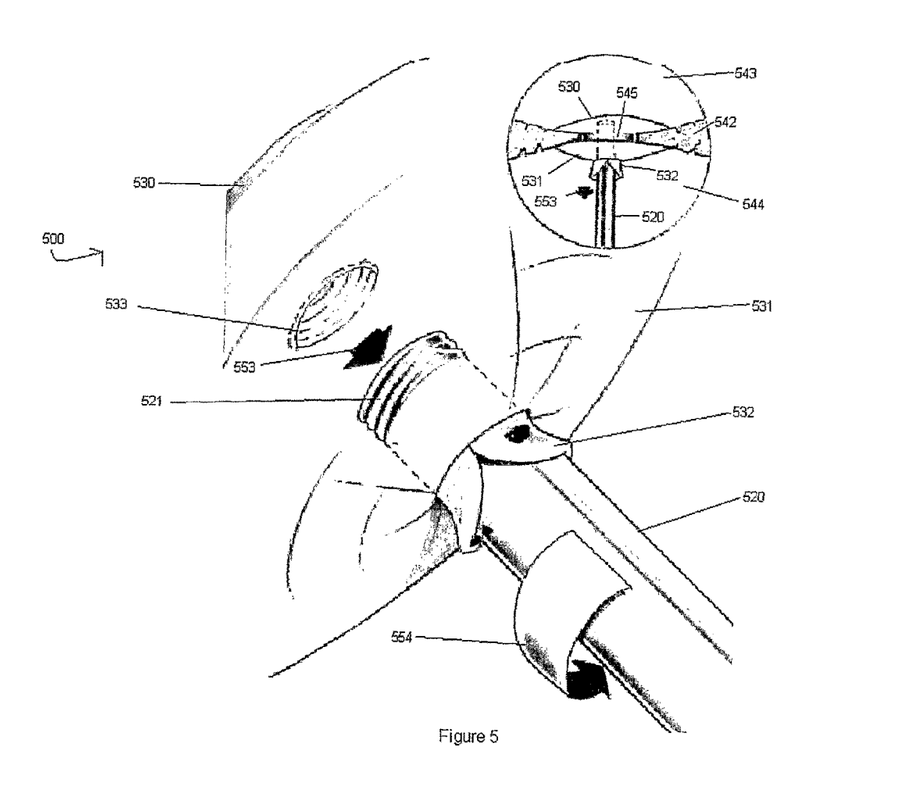
FIG. 5 shows a front view of a magnetic device with a catheter being unscrewed from a proximal magnetic occluder after proper positioning of both occluders around the septal hole or rupture according to an exemplary embodiment of the present invention.

The next step of use of an exemplary embodiment of the present invention as used in a magnetic assembly 500 is shown in FIG. 5. After the proximal magnetic occluder 530 is positioned on the surface of the septum 542 of the left atrium or ventricle 543 and the distal magnetic occluder 531 is positioned on the surface of the septum 542 of the right atrium or ventricle 544, the catheter 520 may be unscrewed from the threaded throughbore 533 of the proximal magnetic occluder 530 by rotating the catheter 520 in a counter-clockwise direction as shown by arrow 554. In this way, the catheter screw tip 521 may be released from the threaded throughbore 533 of the proximal magnetic occluder 530 and the user may pull the catheter 520 out of the proximal magnetic occluder 530 as shown by arrow 553.

To make sure that the distal magnetic occluder 531 does not shift during the disconnection process, the user may continue to exert force on the stabilizer (not shown) such that the distal magnetic occluder 531 remains attached to the surface of the septum 542 on the right atrial or ventricular side 544. Then, the user may continue to unscrew the catheter screw tip 521 in the same manner as above from the threaded throughbore (not shown) of the distal magnetic occluder 531 thereby releasing the distal magnetic occluder 531 from the catheter 520. Additionally, both threaded throughbores may possess flaps 532 made of any suitable biocompatible polymer (e.g., Dacron or polytetrafluoroethylene). These flaps 532 may be situated on both the proximal and distal surfaces of both magnetic occluders such that the flaps prevent fluid from passing though the threaded throughbores 533 after the catheter 520 is removed from both magnetic occluders. Thus, the flaps 532 may be of such a diameter (e.g., equivalent to the diameter of threaded throughbores 533) and of such a design (e.g., slitted) such that when then catheter 520 is removed from both magnetic occluders, the flaps 532 may effectively prevent blood or any other fluid from passing through the threaded throughbores 533 of the magnetic occluders. Thus, a leak-free barrier may be established between the proximal surface of the proximal magnetic occluder 530 and the distal surface of the distal magnetic occluder 531.

Figure 6:
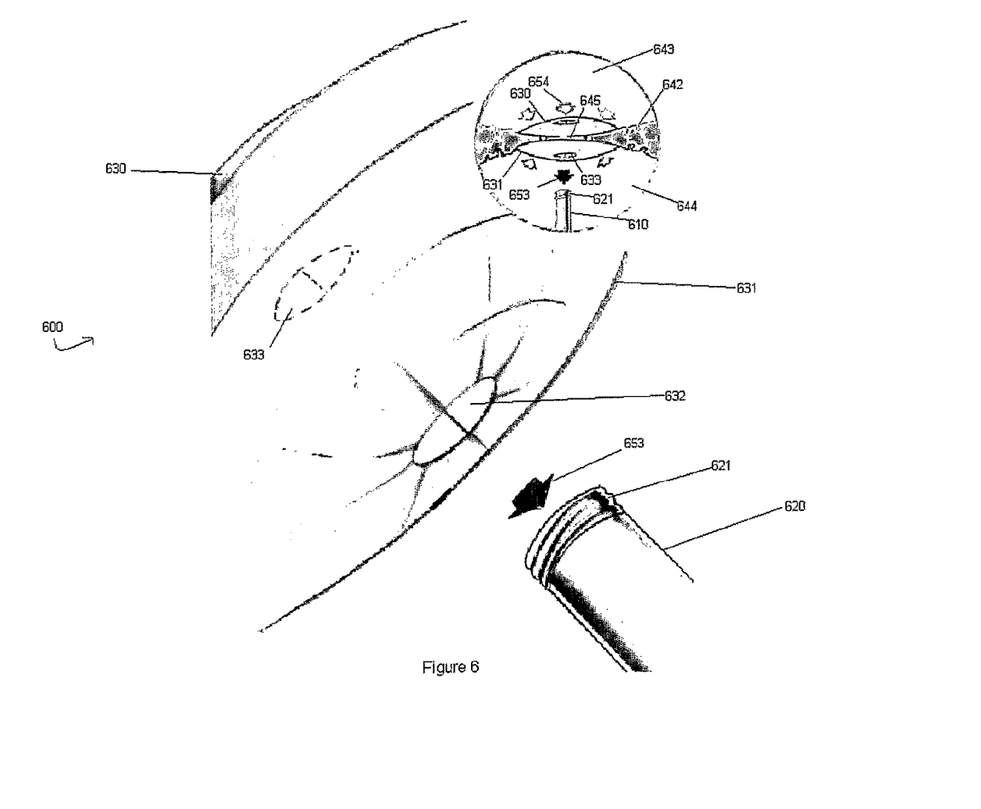
FIG. 6 shows a front view of a magnetic device according to an exemplary embodiment of the present invention after successful implantation with a flap closing to prevent fluid from leaking through the magnetic device.

Finally, the successful deployment of the exemplary embodiment of the present invention as used in magnetic assembly 600 is shown in FIG. 6. After the successful deployment of the proximal magnetic occluder 630 and the distal magnetic occluder 631 to form a leak-free seal covering the hole or rupture 645, the catheter 620 may be completely removed from both magnetic occluders and the flap 632 may thereafter close so as to form an impenetrable barrier for fluid to pass through.

Figure 7:
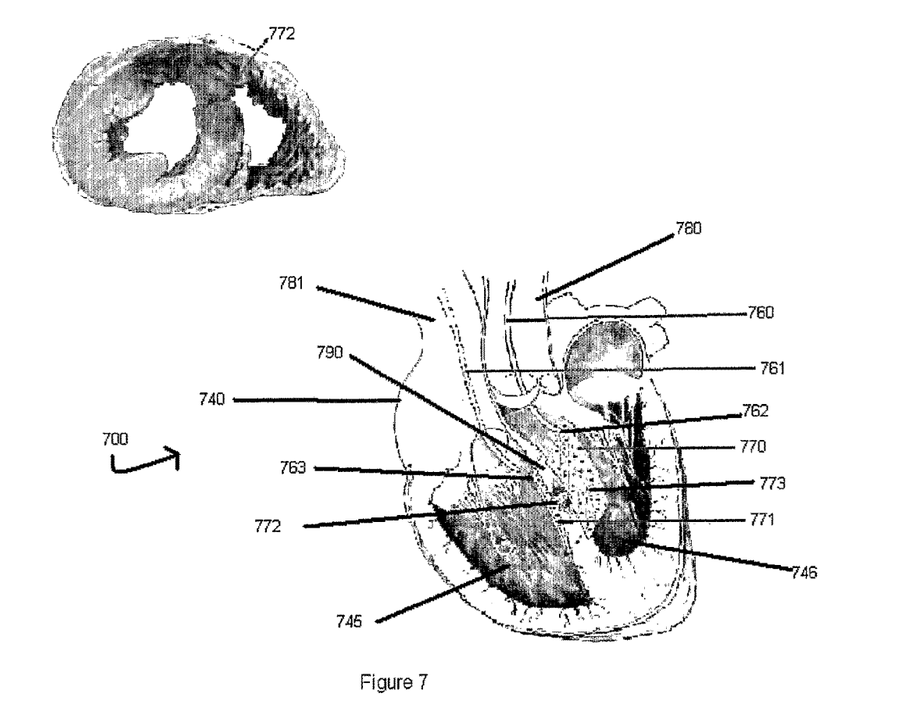
FIG. 7 shows a frontal section of a heart revealing the location of a magnetic device that includes two opposed patches to close a ventricular septal rupture according to an exemplary embodiment of the present invention.

Another exemplary embodiment of the present invention as used in magnetic assembly 700 is shown in FIG. 7. Assembly 700 includes left catheter 760, right catheter 761, first patch 770, and second patch 771 situated inside the heart 740. The left catheter 760 may have attached the first patch 770 at is distal end via attachment site 762 as shown in FIG. 7. In order to ensure that the first patch 770 does not detach from the left catheter 761 during insertion of the first patch 770, the left catheter 760 may have a non-magnetic screw tip (not shown) which may mate with a threaded opening (not shown) in the first patch 770 such that the user is able to unscrew and detach the first patch 770 from the left catheter 760 after the first patch 770 is positioned on the surface of the left side of the ventricular septum 790. This attachment method may be similar to the method described above. The same attachment method may be used for attachment site 763 to attach the second patch 771 to the right catheter 761. The second patch 771 is shown as being disconnected from the right catheter 761 in FIG. 7 after being properly positioned on the surface of the right side of the ventricular septum 790.

Various techniques and methods may be used to introduce the patch 770 through the catheter. Some of these techniques are apparent to one having ordinary skill in the art after consideration of the present disclosure. Other novel techniques are also possible. For example, reference is made to copending application PCT/US06/29425, entitled "Devices and Methods for Percutaneous Endo-Ventricular Reconstruction of the Failing Heart," filed simultaneously on 28 Jul. 2006, which content is hereby incorporated by reference herein in its entirety, in order to provide alternative exemplary delivery methods for the present invention.

In the copending application, a delivery method is disclosed which may be used for the present invention and includes a catheter attached to a rolled magnetic film. The rolled magnetic film may be situated underneath a covering. When the rolled magnetic film is exposed from underneath the covering, the magnetic firm may assume a flattened shaped. Another exemplary delivery method is also disclosed in the copending application which involves inflatable balloons having magnetic particles attached to their surfaces. The inflatable balloons may be compressed by a surrounding covering. When the inflatable balloons are exposed from underneath the covering, the inflatable balloons may expand and assume their positions adjacent to the ventricular septum of the heart. Reference to the copending application is meant to illustrate exemplary delivery methods for the present invention and is not the extent of the techniques that may be used to deliver the patch as described in the present application. The present invention may also be introduced endovascularly via any conventional method apparent to one skilled in the art of medical catheterization.

The first patch 770 and the second patch 771 may be flat and rectangular in shape as shown in FIG. 7 or they may be of any other geometric shape (e.g., circular, triangular) such that they form a leak-free closure of the uniquely shaped hole or rupture 772 once positioned on either side of the hole or rupture 772. The patches may have other shapes as well, such as—semicircular, elliptical, round-shape, etc., which depend partially upon the ventricular septal anatomy and the localization of the hole or rupture 772 (e.g. anterior or posterior; simple or complex). The first patch 770 and the second patch 771 may be composed entirely of any magnetic material commonly used in the medical arts or the patches may only possess a magnetic coating on their inner surfaces which physically contact the tissue while the rest of the patches may be composed of any suitable biocompatible non-reabsorbable polymer commonly used in the medical arts. Alternatively, the second patch 771 may be composed of any metal commonly used in the medical arts such that when it is positioned juxtaposed to the first patch 770 which may be composed of magnetic material, there is a sufficiently strong magnetic field to secure the two patches on either side of the ruptured or defective tissue. Additionally, both the first patch 770 and the second patch 771 may contain barbs or other projections (not shown) on their inner surfaces to increase the stabilization of the device on either side of the target tissue and also to assist in the implantation procedure. Both patches may also possess a covering layer of PTFE, Dacron, polyurethane, pericardium, reabsorbable polymers, etc.

During implantation, the first patch 770 and the second patch 771 may be positioned on either side of the ventricular septum 790 via simultaneous catheterization through both the aorta 780 and the superior vena cava 781 as shown in FIG. 7. Alternatively, the first patch 770 may be implanted through the superior vena cava 781 and the second patch 771 may be implanted through the aorta 780 thereby switching the positioning of the patches as shown in FIG. 7. Thus, it does not matter which patch is on which side of the ventricular septum 790 so long as they are in magnetic communication with one another across the ventricular septum 790. Alternatively, the first patch 770 may be implanted first before the second patch 771 and such a 2-step implantation process would be facilitated by the presence of barbs or extensions (not shown) on the inner surface of both patches. Either way, assembly 700 may act to prevent fluid communication between the right ventricle 745 and the left ventricle 746 and may prevent leakage of blood 773 through the ventricular septum 790.

The above described exemplary embodiment of the present invention can be used for patients with acute IVSD post AMI (anterior or posterior) or in high risk patients that reveal cardiogenic shock, acute pulmonary edema, right and left ventricular infarction, etc. The catherization procedure as described above and shown in FIG. 7 may be used as a biventricular catheterization (right ventricle through percutaneous internal jugular or femoral vein approach and left ventricle through percutaneous femoral or brachial artery) for septal occlusion. This allows simultaneous delivery of magnetic patches to close the interventricular septal defect (single or multiple) post-acute myocardial infarction (sandwich effect) as shown in FIG. 7. In a similar fashion, the assembly 700 can correct defects in the ventricular septum 790, such as leaky septa in patients with infarcts and other conditions. Such mechanical force and support as provided by the exemplary embodiment of the present invention shown in FIG. 7 allows for the decreasing or preventing of the septal leakage and any further growth of interventricular hole(s).

There are a number of advantages associated with this device and method including but not limited to: (1) percutaneous approach through right and left catheterization, (2) simultaneous delivery of wide covered magnetic stent patch in the right and left interventricular septum faces (sandwich effect), (3) easy and fast insertion under local anesthesia, (4) allows rapid and extensive closure and support of the interventricular septum rupture (simple or complex multi-perforation), (5) allows of rapid hemodynamic stabilization decreasing or totally interrupting the transeptal shunt, (6) avoids residual (post surgical or the appearance of new perforations due to progressive extension of the necrotic tissue), and (7) evaluation of the exclusion procedure with TE Echo, x-Ray or angiography.

For the above disclosure, in the absence of expressly defined materials to be used for stated components, it may be assumed that the components may be comprised of any suitable biocompatible non-resorbable polymer such that the component may function as described.

The manufacturing methods that can be employed for the present invention include, but are not limited to, conventional techniques used in the industry to produce similar function products, as known by a person having ordinary skill in the art.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

The invention claimed is:

1. A method, comprising the steps of:
endovascularly introducing at least part of a device into the patient, the device comprising:
an elongate covering,
a catheter positioned at least partially within the covering, the catheter having a first occluder removably affixed thereto and a second occluder slidably engaged upon the catheter, the first occluder located proximal of the second occluder, the second occluder comprising a throughbore, the throughbore possessing flaps that prevent fluid from passing through the throughbore and are configured to form a leak-free barrier, and
a stabilizer positioned at least partially around the catheter;
advancing the device within a vasculature of the patient so that the first occluder, when discharged from an opening of the elongate covering, is positioned through an aperture of a septum and is located distal to the septum against the septum;
moving the stabilizer relative to the elongate covering so to discharge the second occluder so that it is located proximal to the septum against the septum and so that the first occluder and the second occluder close the aperture; and
removing the catheter from the vasculature;
wherein the method is performed to treat a condition of the patient.

2. The method of claim 1, wherein the condition comprises cardiogenic shock.

3. The method of claim 1, wherein the first occluder is magnetically attracted to the second occluder.

4. The method of claim 1, performed to decrease leakage of blood through the aperture of the septum.

5. The method of claim 1, performed to prevent further growth of the aperture.

6. A device, comprising:
an elongate covering;
a catheter positioned at least partially within the covering, the catheter having a first occluder removably affixed thereto and a second occluder slidably engaged upon the catheter, the first occluder located proximal of the second occluder, the second occluder comprising a throughbore, the throughbore possessing flaps that prevent fluid from passing through the throughbore and are configured to form a leak-free barrier;
a stabilizer positioned at least partially around the catheter; and wherein the first occluder and the second occluder, when positioned on opposite sides of a septum and covering an opening of the septum, decrease blood flow through the opening.

7. The device of claim 6, wherein the first occluder and the second occluder are configured to expand after being discharged from an opening of the elongate covering.

8. The device of claim 6, configured for percutaneous insertion and intravascular delivery to the septum.

9. The device of claim 6, further comprising:
a sensor coupled thereto, the sensor configured to detect a blood oxygen concentration.

10. The device of claim 6, configured to obtain a blood sample from a patient using the catheter after at least part of the device has been percutaneously inserted into the patient.

11. The device of claim 10, wherein the catheter comprises a proximal end and at least one opening, the at least one opening situated at the proximal end of the catheter and located on a lateral surface of the catheter.

12. The device of claim 11, wherein the at least one opening is situated between the first occluder and the second occluder.

13. The device of claim 6, further comprising flaps situated on the first occluder such that the flaps prevent fluid from passing through the first occluder.

14. The device of claim 6, wherein the first occluder comprises a magnetic material and the second occluder comprises a metallic material attracted to the magnetic material.

15. The device of claim 6, wherein the first occluder comprises a threaded throughbore and a proximal end of the catheter is threaded.

16. The device of claim 6, wherein the catheter comprises a non-magnetic screw tip.

17. A device, comprising:

an elongate covering;

a catheter positioned at least partially within the covering, the catheter having a first occluder removably affixed thereto and a second occluder slidably engaged upon the catheter, the first occluder and the second occluder each possessing a throughbore, the throughbores possessing flaps, and the flaps preventing fluid from passing through the throughbores;

a stabilizer positioned at least partially around the catheter;

wherein the first occluder and the second occluder, when positioned on opposite sides of a septum and covering an opening of the septum, decrease blood flow through the opening; and wherein the first occluder and the second occluder are in a compressed shape when within the covering and in an expanded form when out of the covering.

18. The device of claim 17, wherein the throughbores are threaded and the catheter comprises a screw tip.

* * * * *